United States Patent
Boots et al.

(10) Patent No.: US 6,881,824 B1
(45) Date of Patent: Apr. 19, 2005

(54) PEPTIDES SUITABLE FOR USE IN ANTIGEN SPECIFIC IMMUNOSUPPRESSIVE THERAPY

(75) Inventors: Anna Maria Helena Boots, Megen (NL); Gusbertus Franciscus Maria Verheijden, Oss (NL)

(73) Assignee: Akzo Nobel N.V., Arnhem (NL)

( * ) Notice: Subject to any disclaimer, the term of this patent is extended or adjusted under 35 U.S.C. 154(b) by 177 days.

(21) Appl. No.: 09/657,757

(22) Filed: Sep. 8, 2000

Related U.S. Application Data

(62) Division of application No. 09/171,705, filed as application No. PCT/EP97/02051 on Apr. 22, 1997, now Pat. No. 6,184,204.

(30) Foreign Application Priority Data

Apr. 24, 1996 (EP) .............................................. 96201106

(51) Int. Cl.[7] ................................................. A61K 38/00
(52) U.S. Cl. ...................... 530/326; 424/185.1; 514/13
(58) Field of Search .................................. 530/327, 326; 424/184.1, 185.1; 514/14, 13

(56) References Cited

FOREIGN PATENT DOCUMENTS

| WO | WO 95 01995 A | 1/1995 |
|---|---|---|
| WO | WO 96 13517 A | 5/1996 |

OTHER PUBLICATIONS

Wendling et al. J. of Immunology vol. 164 2711–2717, 2000.*

Tisch et al. P.N.A.S. vol. 91. pp. 437–438, 1994.*

Wraith et al. Cell vol. 59, pp. 247–255, 1989.*

Hakala et al. J.B.C. vol. 268, No. 34, pp. 25803–25810, 1993.*

Nyirkos et al., "Human Synovial Cells Secrete a 39 kDa Protein Similar to a Bovine Mammary Protein Expressed During the Non–lactating Period," Biochem. Journal, 1990, vol. 269, pp. 265–268.

Hakala et al., "Human Cartilage gp–39, a Major Secretory Product of Articular Chondrocytes and Synovial Cells, Is a Mammalian Member of a Chitinase Protein Family," J. Bio. Chem., 1993, vol. 268, pp. 25803–25810.

* cited by examiner

*Primary Examiner*—Patrick J. Nolan
(74) *Attorney, Agent, or Firm*—William P. Ramcy, III

(57) ABSTRACT

This invention relates to peptides consisting of 16 to 55 amino acids, said peptides comprising at least one of the amino acid sequences LVCYYTSWS (SEQ ID NO:60), FLCTHIIYS (SEQ ID NO:61), IIYSFANIS (SEQ ID NO:62), LKTLLSVGG (SEQ ID NO:63), FIKSVPPFL (SEQ ID NO:64), FDGLDLAWL (SEQ ID NO:65), LYPGRRDKQ (SEQ ID NO:66), YDIAKISQH (SEQ ID NO:67), LDFISIMTY (SEQ ID NO:68), FISIMTYDF (SEQ ID NO:69), FRGQEDASP (SEQ ID NO:70), YAVGYMLRL (SEQ ID NO:71), MLRLGAPAS (SEQ ID NO:72), LAYYEICDF (SEQ ID NO:73), LRGATVHRT (SEQ ID NO:74), YLKDRQLAG (SEQ ID NO:75), LAGAMVWAL (SEQ ID NO:76), VWALDLDDF (SEQ ID NO:77) or LDLDDFQGS (SEQ ID NO:78). The peptides can be used in the treatment of T cell-mediated destruction of articular cartilage. Administration of pharmaceutical compositions based on these peptides can be used to induce systemic immunological tolerance to the autoantigens under attack of the autoreactive T-cells.

6 Claims, No Drawings

PEPTIDES SUITABLE FOR USE IN ANTIGEN SPECIFIC IMMUNOSUPPRESSIVE THERAPY

This application is a division of U.S. application Ser. No. 09/171,705, filed on Oct. 23, 1998, now U.S. Pat. No. 6,184,204 which is the national stage of PCT/EP97/02051, filed on Apr. 22, 1997.

FIELD OF THE INVENTION

The invention relates to peptides and their use in treatment of chronic destruction of articular cartilage in autoimmune diseases, pharmaceutical compositions comprising said peptides, a diagnostic method for the detection of autoreactive T cells in a test sample and test kits to be used in said method.

BACKGROUND OF THE INVENTION

The immune system is established on a principle of discrimination between foreign antigens (non-self antigens) and autoantigens (self antigens, derived from the individuals own body) achieved by a build in tolerance against the autoantigens.

The immune system protects individuals against foreign antigens and responds to exposure to a foreign antigen by activating specific cells such as T- and B lymphocytes and producing soluble factors like interleukins, antibodies and complement factors. The antigen to which the immune system responds is degraded by the antigen presenting cells (APCs) and a fragment of the antigen is expressed on the cell surface associated with a major histocompatibility complex (MHC) class II glycoprotein. The MHC-glycoprotein-antigen-fragment complex is presented to a T cell which by virtue of its T cell receptor recognizes the antigen fragment conjointly with the MHC class II protein to which it is bound. The T cell becomes activated i.e. proliferates and/or produces interleukines, resulting in the expansion of the activated lymphocytes directed to the antigen under attack (Grey et al., Sci. Am., 261:38–46, 1989).

Self antigens are also continuously processed and presented as antigen fragments by the MHC glycoproteins to T cells (Jardetsky et al., Nature 353:326–329, 1991). Self recognition thus is intrinsic to the immune system. Under normal circumstances the immune system is tolerant to self antigens and activation of the immune response by these self antigens is avoided.

When tolerance to self antigens is lost, the immune system becomes activated against one or more self antigens, resulting in the activation of autoreactive T cells and the production of autoantibodies. This phenomenon is referred to as autoimmunity. As the immune response in general is destructive, i.e. meant to destroy the invasive foreign antigen, autoimmune responses can cause destruction of the body's own tissue.

The contribution of T cells to autoimmune diseases has been established by several studies. In mice, experimental autoimmune encephalomyelitis (EAE) is mediated by a highly restricted group of T cells, linked by their specificity for a single epitope of myelin basic protein (MBP) complexed to an MHC class II molecule. In the Lewis rat, a species with high susceptibility to various autoimmune diseases, disease has been shown to be mediated by T cells.

In humans autoimmune diseases are also thought to be associated with the development of auto-aggressive T cells. A destructive autoimmune response has been implicated in various diseases such as rheumatoid arthritis (RA), in which the integrity of articular cartilage is destroyed by a chronic inflammatory process. The mere presence of cartilage appears necessary for sustaining the local inflammatory response: it has been shown that cartilage degradation is associated with the activity of cartilage-responsive autoreactive T cells in RA (Sigall et al., Clin. Exp. Rheumat. 6:59, 1988; Glant et al., Biochem. Soc. Trans. 18:796, 1990; Burmester et al., Rheumatoid arthritis Smolen, Kalden, Maini (Eds) Springer-Verlag Berlin Heidelberg, 1992) Furthermore, removal of cartilage from RA patients by surgery was shown to reduce the inflammatory process. The cartilage proteins are therefore considered to be target autoantigens which are competent of stimulating T cells. Activation of these autoreactive T cells leads to development of autoimmune disease. Hence it can be anticipated that functional elimination of these T cells could be beneficial in downregulation of the destructive autoimmune process. However, the identification of the autoantigenic components that play a role in the onset of rheumatoid arthritis has so far remained elusory.

The inflammatory response resulting in the destruction of the cartilage can be treated by various drugs. However, these drugs are immunosuppressive drugs that are nonspecific and have toxic side effects. The disadvantages of nonspecific immunosuppression makes this a highly unfavorable therapy Antigen-specific, nontoxic immunosuppression, such as for instance described in WO-A-9510301, provides a very attractive alternative for nonspecific immunosuppression. The antigen-specific therapy involves the treatment of patients with synthetic T cell-reactive peptides which resemble or mimic the epitopes present on the autoantigen. These peptides can therefore be used to induce systemic immunological tolerance, i.e. specific T cell tolerance, both to themselves and to the autoantigen. The induced systemic immunological tolerance is based on the long-observed phenomenon that animals which have been fed or have inhaled an antigen or epitope are less capable of developing a systemic immune response towards said antigen or epitope when said antigen or epitope is introduced via a systemic route. To effectively use the peptide-induced systemic tolerance therapy to treat the T cell mediated cartilage destruction, there is no great need for T cell-reactive peptides which can desensitize patients against the self antigen that is activating the T cells responsible for the inflammatory process.

It is an object of the invention to provide peptides which are able to induce systemic immunological tolerance, more in particular specific T cell tolerance, to the responsible cartilage antigen in patients suffering from T cell-mediated cartilage destruction. It is another object of the invention to provide a method for detecting autoreactive T cells involved in the destruction of articular cartilage and test kits to be used in said method.

The present invention provides for such peptide.

In a first aspect of the invention there is provided for peptides consisting of 16 to 55 amino acid residues, said peptide comprising at least one of the amino acid sequences LVCYYTSWS (SEQ ID NO:60), FLCTHIIYS (SEQ ID NO:61), IIYSFANTS (SEQ ID No:62), LKTLLSVGG (SEQ ID NO:63), FIKSVPPFL (SEQ ID NO:64), FDGLD-LAWL (SEQ ID NO: 65), LYPGRRDKQ (SEQ ID No:66), YDIAKISQH (SEQ ID NO:67), LDFISIMTY (SEQ ID NO:68), FISIMTYDF (SEQ ID NO:69), FRGOEDASP (SEQ ID NO:70), YAVGYMLMRL, (SEQ ID NO:71), MLRLGAPAS (SEQ ID NO:72), LAYYEICDF (SEQ ID NO:73), LRGATVHRT (SEQ ID NO:74), YTKDRQLAG (SEQ ID NO:75), LAGAVWAL (SEQ ID NO:76), VWALDLDDF (SEQ ID NO:77) or LDLDDFQGS (SEQ ID NO:78).

In particular, the peptide according to the invention comprises at least one of the amino acid sequence YKLVCYYTSWSQYREG (SEQ ID NO:1), YTSWSQYREGDGSCFP (SEQ ID NO:2), LDRFLCTHIIYSFANI (SEQ ID NO:5), THIIYSFANISNDHID (SEQ ID NO:6), NLTLLSVGWNFGS (SEQ ID NO:12), NTQSRRTFIKSVPPFL (SEQ ID NO:16), TFIKSVPPFLRTHGFD (SEQ ID NO:17), PPFLRTHGFDGLDLAW (SEQ ID NO:18), HGFDGLDLAWLYPGRR (SEQ ID NO:19), DLAWLYPGRRDKQHFT (SEQ ID NO:20), TIDSSYDIAKISQHLD (SEQ ID NO:28), DIAKISQHLDFISIMT (SEQ ID NO:29), QHLDFISIMTYDPHGA (SEQ ID NO:30), SPLFRGQEDASPDRFS (SEQ ID NO:34), DYAVGYMLRLGAPASK (SEQ ID NO:37), MLRLGAPASKLVMGIP (SEQ ID NO:38), PASKLVMGIPTFGRSF (SEQ ID NO:39), GTLAYYEICDFLRGAT (SEQ ID NO:46), EICDFLRGATVHRTLG (SEQ ID NO:47), RGATVHRTLGQQVPYA (SEQ ID NO:48), VKSKVQYLKDRQLAGA (SEQ ID NO:53), YLKDRQLAGAMVWALD (SEQ ID NO:54), LAGAMVWALDLDDFQG (SEQ ID NO:55), WALDLDDFQGSFCGQD (SEQ ID NO:56) or DFQGSFCGQDLRFPLT (SEQ ID NO:57).

Preferably, the peptide according to the present invention comprises one of the amino acid sequences YKLVCYYTSWSQYREG (SEQ ID NO:1), YTSWSQYREGDGSCFP (SEQ ID NO: 2) LDRFLCTHIIYSFANI (SEQ ID NO:5), THIIYSFANISNDHID (SEQ ID NO 6), PNLKTLLSVGGWNFGP (SEQ ID NO:12), QHLDFISIMTYDFHGA (SEQ ID NO:30), SPLFRGOEDASPDRPS (SEQ ID No:34), DYAVGYMLRLGAPASK (SEQ ID NO:37), MLRLGAPASKLVMGIP (SEQ ID NO:38), YLKDRQLAGAMVWALD (SEQ ID NO:54) or LAGAMVWALDLDDFQG (SEQ ID NO:55).

More preferably, the peptide according to the invention comprises one or more of the amino acid sequences YTSWSQYREGDGSCFP (SEQ ID NO:2), SPLFRGQEDASPDRFS (SEQ ID NO:34), MLRLGAPASKLVMGIP (SEQ ID NO:38), YLKDRQLAGAMVWALD (SEQ-ID NO:54) or LAGAMVWALDLDDFQG (SEQ ID NO:55).

The peptides according to the invention consist of 16 to 55, preferably 16 to 35, more preferably 16, to 25, most preferably 16 amino acid residues.

Highly preferred peptides according to the invention are hexadecapeptides consisting of the amino acid sequence YKLVCYYTSWSQYREG (SEQ ID NO:1) YTSWSQYREGDGSCFP (SEQ ID NO:2) LDRFLCTHIIYSFANI (SEQ ID NO:5), THIIYSFANISNDHID (SEQ ID NO 6). PNLKTLLSVGGWNFGS (SEQ ID NO:12), QHLDFISIMTYDFHGA (SEQ ID NO:30), SPLFRGQEDASPDRFS (SEQ ID NO:34), DYAVGYMLRLGAPASK (SEQ ID NO:37), MLRLGAPASKLVMGIP (SEQ ID NO:38), YLKDRQLAGAMVWALD (SEQ ID NO:54) or LAGAMVWALDLDDFQG (SEQ ID NO:55), more in particular the amino acid sequences YTSWSQYREGDGSCFP (SEQ ID NO:2), SPLFRGQEDASPDRFS (SEQ ID NO:34), MLRLGAPASKLVMGIP (SEQ ID NO:38), YLKDRQLAGAMVWALD (SEQ ID NO:54) or LAGAMVWALDLDDFQG (SEQ ID NO:55)

Also within the scope of the invention are multimers of the peptides according to the invention such as for example a dimer or trimer of the peptides according to the invention A multimer according to the invention can either be a homomer, consisting of a multitude of the same peptide, or a heteromer consisting of different peptides.

The characteristic amino acid sequences of the peptides according to the invention can be flanked by random amino acid sequences. Preferred are flanking sequences, that have a stabilizing effect on the peptides, thus increasing their biological availability.

The present invention is based on the unexpected discovery, that Human Cartilage glycoprotein 39 (herein after referred to as HC gp-39) is a target autoantigen in RA patients which activates specific T cells, thus causing or mediating the inflammatory process. HC gp-39 derived peptides were predominantly recognized by autoreactive T cells from RA patients but rarely by T cells from healthy donors, thus indicating that HC gp-39 is an autoantigen in RA. The arthritogenic nature of HC gp-39 was further substantiated in the Balb/c mouse. A single, subcutaneous injection of said protein in Balb/c mice was able to initiate arthritic signs in the animals. The course of the HC gp-39-induced disease was characterized by relapses occurring periodically in fore paws and/or hind paws and gradually developed from a mild arthritis into a more severe form. Also, a symmetrical distribution of afflicted joints was observed which is, together with the observation of recurrent relapses and nodule formation, reminiscent of disease progression in arthritis, especially RA.

Even more surprisingly it was found that administration of HC gp-39 resulted in immunological tolerance and, more importantly, in delayed and/or suppressed arthritic development.

The amino acid sequences given in SEQ ID NO's 60–78, more specifically the sequences given in SEQ ID NO's 1, 2, 5, 6, 12, 16–20, 28–30, 34, 37–39, 46–48, 53 –57 resemble MHC class II restricted T cell epitopes which are present on HC gp-39. Thus, the peptides according co the invention can also be understood to encompass fragments of the autoantigen HC gp-39 which comprise one or more of the above identified MHC Class II restricted T-cell epitopes and they are also within the scope of the invention.

Although HC gp-39 was disclosed in Hakala et al., J. Biol. Chem., Vol. 268, No. 34, 25803 (1993), in which it was described as a chitinase protein and suggested for use as a suitable marker for rheumatoid arthritis, any hint or suggestion towards the arthritogenic nature of HC gp-39 was absent.

The peptides according to the invention can be prepared by well known organic chemical methods for peptide synthesis such as, for example, solid-phase peptide synthesis described for instance in J. Amer. Chem. Soc. 85.2149 (1963) and Int. J. Peptide Protein Res. 35:161–214 (1990).

The peptides according to the invention can also red by recombinant DNA techniques. A nucleic acid sequence coding for a peptide according to the invention or a multimer of said peptides is inserted into an expression vector. Suitable expression vectors are, amongst others, plasmids, cosmids, viruses and YAC's (Yeast Artificial Chromosomes) which comprise the necessary control regions for replication and expression. The expression vector can be brought to expression in a host cell. Suitable host cells are, for instance, bacteria, yeast cells and mammalian cells. Such techniques are well known in the art, see for instance Sambrooke et al, Molecular Cloning: a Laboratory Manual, Cold Spring Harbor laboratory Press, Cold spring Harbor, 1989.

The peptides according to the invention are T-call reactive peptides, which are recognized by and are able to stimulate activated, autoreactive T-cells. These autoreactive T cells are found in the blood of RA patients but rarely ill healthy donors.

Thus, according to the invention the synthetic peptides, said peptides resembling the MHC Class II restricted W-cell epitopes present on the target autoantigen HC gp-39, are very suitable for use in a therapy to induce specific T-cell tolerance to HC gp-39 in mammals, more specifically humans, suffering from T-cell mediated cartilage destruction, such as for example arthritis, more specifically rheumatoid arthritis.

Although WO 95/01995 and WO 95/02188 describe the diagnostic use of HC gp-39 as a marker for RA, the arthritogenic nature of HC gp-39 is neither disclosed nor suggested. Nowhere do they hint or suggest towards the use of fragments of HC gp-39 or T-cell reactive peptides according to the present invention in the antigen or peptide specific therapy to induce T-cell specific tolerance to the HC gp-39 in the cartilage under attack.

According to the invention, patients suffering from T-cell mediated destruction of the articular cartilage can be treated with a therapeutical composition comprising one or more peptides according to the invention and a pharmaceutical acceptable carrier. Administration of the pharmaceutical composition according to the invention will induce systemic immunological tolerance, in particular tolerance of the specific autoreactive T cells of these patients, to the autoantigenic proteins in the articular cartilage under attack and other self antigens which display the identified MHC Class II binding T cell epitopes characterized or mimiced by the amino acid sequences of one or more of the peptides according to the invention. The induced tolerance thus will lead to a reduction of the local inflammatory response in the articular cartilage under attack.

Very suitable peptides to be used in a pharmaceutical composition according to the invention are the peptides having 16–55, preferably 16–35, more preferably 16–25, most preferably 16 amino acid residues, said peptides comprising at least one of the amino acid sequences LVCYYTSWS (SEQ ID NO:60)FLCTHIIYS (SEQ ID NO:61), IIYSFANIS (SEQ ID NO:62), LKTLLSVGC (SEQ ID NO:63), FIKSVPPFL (SEQ ID NO:64), FDGLDLAWL (SEQ ID NO: 65), LYPGRRDKQ (SEQ ID NO:66), YDIAKISQH (SEQ ID NO:67), LDFISIMTY (SEQ ID NO:68), FISIMTYDF (SEQ ID NO:69). FRGOEDASP (SEQ ID NO:70), YAVGYMLRL (SEQ ID NO:71), MLRLGAPAS (SEQ ID NO:72), LAYYEICDF (SEQ ID NO:73), LRGATVHRT (SEQ ID NO:74), YLKDRQLAG (SEQ ID NO:75), LAGAMVWAL (SEQ ID NO:76), VWALDLDDF (SEQ ID NO:77) or LDLDDFQGS (SEQ ID NO:78) more in particular one of the amino acid sequences YCLVCYYTSWSQYREG (SEQ ID NO:1), YTSWSOYREGDGSCFP (SEQ ID NO: 2), LDRFLCTHIIYSFANI (SEQ ID NO:5), THIISYSFANISNDHID (SEQ ID NO:6), PNLKTLLSVGGWNFGS (SEQ ID NO:12) NTQSRRTFIKSVPPFL (SEQ ID NO:16), TFIKVPPFLRTHFGD (SEQ ID NO:17), PPFLRTHGFDGLDLAW (SEQ ID NO:18), HGFDGLDLAWYPGRR (SEQ ID NO:19), DLAWLYPGRRDKQHFT (SEQ ID NO:20), TIDSSYDIAKISQHLD (SEQ ID NO:28), DIAKISQHLDFISIMT (SEQ ID NO:29), QHLDFISIMTYDFHCGA (SEQ ID NO: 30), SPLFRGOEDASPORRFS (SEQ ID NO:34), DYAVGYMLRLGAPASK (SEQ ID NO:37), MLRLGAPASKLVMGIP (SEQ ID NO:38), PASKLVMGIPTFGRSF (SEQ ID NO:39), GTLAYYEICDFLRGAT (SEQ ID NO:46), EICDFLRGATVHRTLG (SEQ ID NO:47), RGATVHRTLGQQVPYA (SEQ ID NO:48), VKSKVQYLKDRQLAGA (SEQ ID NO:53), YLKDRQLAGAMVWALD (SEQ ID NO:54), LAGAMVWALDLDDFQG (SEQ ID NO:55), WALDLDDFQGSFCGQD (SEQ ID NO:56) or DFQGSFCGQDLRFPLT (SEQ ID NO:57).

Specifically preferred in a pharmaceutical composition according to the invention are the peptides having 16–55, preferably 16–35, more preferably 16–25, most preferably 16 amino acid residues, said peptides comprising at least one of the amino acid sequences YKLVCYYTSWSQYREG (SEQ ID NO:1), YTSWSQYREGDGSCFP (SEQ ID NO:2), LDRFLCTHIIYSFANI (SEQ ID NO:5), THIIYSFANISNDHID (SEQ ID NO:6), PNLKTLLSVGGWNFGS (SEQ ID NO:12), QHLDFISIMTYDFHGA (SEQ ID NO:30), SPLFRGQEDASPDRFS (SEQ ID NO:34), DYAVGYMLRLIGAPASK (SEQ ID NO:37), MLRLGAPASKLVMGIP (SEQ ID NO:38), YLKDRQLAGAMVWALD (SEQ ID NO:54) or LAGAMVWALDLDDFQG (SEQ ID NO:55).

Highly preferred in a pharmaceutical composition according to the invention are peptides having 16–55, preferably 16–35, more preferably 16–25, most preferably 16 amino acid residues, said peptides comprising at least one of the amino acid sequences YTSWSQYREGDGSCFP (SEQ ID NO:2), SPLFRGQEDASPDRFS (SEQ ID NO:34), MLRLGAPASKLVMGIP (SEQ ID NO:38), YLKDRQLAGAMVWALD (SEQ ID NO:54) or LAGAMVWALDLDDFQG (SEQ ID NO:55).

Most preferred in a pharmaceutical composition according to the invention are hexadecapeptides consisting of the amino acid sequence YKLVCYYTSWSQYREG (SEQ ID NO:1) YTSWSQYREGDSGFP (SEQ ID. NO:2), LDRFLCTHIIYSFANI (SEQ ID NO:5), THIIYSFANISNHID (SEQ. ID NO:6), PNLKTLLSVGGWNFGS (SEQ ID NO:12), QHLDFISIMTYDFHGA (SEQ ID NO:30), SPLFRGQEDASPDRFS (SEQ ID NO:34), DYAVGYMLRLGAPASK (SEQ ID NO:37), MLRLGAPASKLVMGIP (SEQ ID NO:38), YLKDRQLAGAMVWALD (SEQ ID NO:54) or LAGAMVWALDLDDFQG (SEQ ID NO:55), more in particular the amino acid sequences YTSWSQYREGDGSCFP (SEQ ID NO:2). SPLFRGQEDASPDRFS (SEQ ID NO:34), MLRLGAPASKLVMGIP (SEQ ID NO:38), YLKDRQLACAMVWALD (SEQ ID NO:54) or LAGAMVWALDLDDFQG (SEQ ID NO:55).

The peptides according to the invention have the advantage that they have a specific effect on the autoreactive T cells thus leaving the other components of the immune system intact as compared to the nonspecific suppressive effect of immunosuppressive drugs. Treatment with the peptides according to the invention will be safe and no toxic side effects will occur.

Systemic immunological tolerance can be attained by administering high or low doses of peptides according to the invention. The amount of peptide will depend on the route of administration, the time of administration, the age of the patient as well as general health conditions and diet.

In general, a dosage of 0.01 to 1000 µg of peptide per kg body weight, preferably 0.5 to 500 µg, more preferably 0.1 to 100 µg of peptide can be used.

Pharmaceutical acceptable carriers are well known to those skilled in the art and include, for example, sterile salin, lactose, sucrose, calcium phosphate, gelatin, dextrin, agar, pectin, peanut oil, olive oil sesame oil and water. Other carriers may be, for example MHC class II molecules, if desired embedded in liposomes.

In addition the pharmaceutical composition according to the invention may comprise one or more adjutants. Suitable adjutants include, amongst others, aluminum hydroxide, aluminum phosphate, amphigen, tocopherols, monophosphenyl lipid A, muramyl dipeptide and saponins such as Quill A. Preferably, the adjutants to be used in the tolerance therapy according to the invention are mucosal adjutants such as the cholera toxine B-subunit or carbomers, which bind to the mucosal epithelium. The amount of adjuvant depends on the nature of the adjuvant itself.

Furthermore the pharmaceutical composition according to the invention may comprise one or more stabilizers such as, for example, carbohydrates including sorbitol, mannitol, starch, sucrosedextrin and glucose, proteins such as albumin or casein, and buffers like alkaline phosphates.

Suitable administration routes are intramuscular injections, subcutaneous injections, intravenous injections or intraperitoneal injections, oral administration and nasal sprays.

The peptides according to the invention are also very suitable for use in a diagnostic method to detect the presence of activated autoreactive T cells involved in the chronic inflammation and destruction of the articular cartilage.

The diagnostic method according to the invention comprises the following steps:
  a) isolation of the peripheral blood mononuclear cells (PBMC) from a blood sample of an individual,
  b) culture said PBMC under suitable conditions,
  c) incubation of said PBMC culture in the presence of one or more peptides according to the invention, and
  d) detection of a response of T cells, for example a proliferative response, indicating the presence of activated autoreactive T cells in the individual.

The detection of a proliferative response of T cells can be detected by, for example, the incorporation of $^3$H-thymidine.

Also within the scope of the invention are test kits which comprise one or more peptides according to the, invention. These test kits are suitable for use in a diagnostic method according to the invention.

The following examples are illustrative for the invention and should in no way be interpreted as limiting the scope of the invention.

EXAMPLES

Methods
Patients

This study included 7 DR4(DRB1*0401)-positive patients diagnosed as suffering from RA according to the ARA criteria (Arnett et al., (1988), Arthritis Rheum. 31, 315). Peripheral blood samples were obtained with informed consent. There were five women and two men aged 46–79 years. Their duration of disease ranged from over 10 to over 30 years. Three out of 7 patients had at least 3 swollen joints. Four patients did not show any signs of active disease. All patients were on medication: Four patients were treated with prednisone, three patients received anti-rheumatic agents and 4 patients were treated with NSAID's as well.

Peripheral blood samples from 5 healthy donors carrying the DR4(DRB1*0401) specificity were obtained with informed consent and included in this study as a control.
Definition of HLA-DR Polymorphisms.

Patient and healthy donor peripheral blood mononuclear cells (PBMC) isolated from heparinized peripheral blood by standard centrifugation on Ficoll-Paque were stimulated with PHA (Welcome, Dartford, UK) to obtain $5 \times 10^6$–$10^7$ lymphocytes. The QIA amp blood kit (QIAGEN Inc,) was used to purify chromosomal DNA from cultured cells according to the manufacturers instruction. Chromosomal DNA extracts were analysed using a DR 'low resolution' SSP kit. DR4 subtyping was performed using the Dynal DRB1*04-SSP kit. MHC DR typing was performed at the Transparent Serology Laboratory, University Hospital, Nijmegen, The Netherlands.

TABLE I

| RA Patient | stage | synovitis | duration | HLA-DR |
|---|---|---|---|---|
| 191 | IV | no | >30 years | 0401/01 |
| 259 | III–IV | yes | >30 years | 0401/16 |
| 262 | III–IV | yes | >10 years | 0401/0408 |
| 272 | III–IV | no | >30 years | 0401/0701 |
| 276 | IV | no | >30 years | 0401/14 |
| 286 | IV | no | 20 years | 0401/0408 |
| 287 | III–IV | yes | 20 years | 0401/13 |
| HD | | | | HLA-DR |
| 155 | | | | 0401/14 |
| 157 | | | | 0401/13 |
| 168 | | | | 0401/07 |
| 230 | | | | 0401/07 |
| 235 | | | | 0401/13 |

Peptide Synthesis

Peptides were synthesized at Eurosequence (Groningen. The Netherlands). Peptides were synthesized from the C-terminus to the N-terminus on a 10 μmol scale using solid-phase FMOC chemistry. The crude peptides were partly purified by several other preparations. As indicated by the manufacturer, at least 35% of the lyophilized product contained the desired full length product. The rest contained salt and remaining solvent. The quality of the final product was checked by sequence analysis, amino acid analysis and/or RF-HPLC. The sequences of the peptides synthesized are enlisted in Table II.

TABLE II

Amino acid sequences of the peptides used in this study.

| SEQ ID NO: | residu | peptide |
|---|---|---|
| 1 | 22–37 | YKLVCYYTSWSQYREG |
| 2 | 28–43 | YTSWSQYREGDGSCFP |
| 3 | 34–49 | YREGDGSCFPDALDRF |
| 4 | 40–55 | SCFPDALDRFLCTHII |
| 5 | 46–61 | LDRFLCTHIIYSFANI |
| 6 | 52–67 | THIIYSFANISNDHID |
| 7 | 58–73 | FANISNDHIDTWEWND |
| 8 | 64–79 | DHIDTWEWNDVTLYGM |
| 9 | 70–85 | EWNDVTLYGMLNTLKN |
| 10 | 76–91 | LYGMLNTLKNRRNPNLK |
| 11 | 82–97 | TLKNRNPNLKTLLSVG |
| 12 | 88–103 | PNLKTLLSVGGWNFGS |
| 13 | 94–109 | LSVGGWNFGSQRFSKI |
| 14 | 100–115 | NFGSQRFSKIASNTQS |
| 15 | 106–121 | FSKIASNTQSRRTPIK |
| 16 | 112–127 | NTQSRRTFIKSVPPFL |
| 17 | 118–133 | TFIKSVPPFLRTHGFD |
| 18 | 124–139 | PPFLRTHGFDGLDLAW |
| 19 | 130–145 | HGFDGLDLAWLYPGRR |
| 20 | 136–151 | DLAWLYPGRRDKQHFT |
| 21 | 142–157 | PGRRDKQHFTTLIKEM |
| 22 | 148–163 | QHFTTLIKEMKAEFIK |
| 23 | 154–169 | IKEMKAEFIKEAQPGK |
| 24 | 160–175 | EFIKEAQPGKKQLLLS |
| 25 | 166–181 | QPGKKQLLLSAALSAG |
| 26 | 172–187 | LLLSAALSAGKVTIDS |
| 27 | 178–193 | LSAGKVTIDSSYDIAK |
| 28 | 184–199 | TIDSSYDIAKISQHLD |
| 29 | 190–205 | DIAKISQHLDFISIMT |
| 30 | 196–211 | QHLDFISIMTYDFHGA |
| 31 | 202–217 | SIMTYDFHGAWRGTTG |

TABLE II-continued

Amino acid sequences of the peptides used in this study.

| SEQ ID NO: | residu | peptide |
|---|---|---|
| 32 | 208–223 | FHGAWRGTTGHHSPLF |
| 33 | 214–229 | GTTGHHSPLFRGQEDA |
| 34 | 220–235 | SPLFRGQEDASPDRFS |
| 35 | 226–241 | QEDASPDRFSNTDYAV |
| 36 | 232–247 | DRFSNTDYAVGYMLRL |
| 37 | 238–253 | DYAVGYMLRLGAPASK |
| 38 | 244–259 | MLRLGAPASKLVMGIP |
| 39 | 250–265 | PASKLVMGIPTFGRSF |
| 40 | 256–271 | MGIPTFGRSFTLASSE |
| 41 | 262–277 | GRSFTLASSETGVGAP |
| 42 | 268–263 | ASSETGVGAPISGPGI |
| 43 | 274–289 | VGAPISGPGIPGRFTK |
| 44 | 280–295 | GPGIPGRFTKEAGTLA |
| 45 | 286–301 | RFTKEAGTLAYYEICD |
| 46 | 292–307 | GTLAYYEICDFLRGAT |
| 47 | 298–313 | EICDFLRGATVHRTLG |
| 48 | 304–319 | RGATVHRTLGQQVPYA |
| 49 | 310–325 | RTLGQQVPYATKGNQW |
| 50 | 316–331 | VPYATKGNQWVGYDDQ |
| 51 | 322–337 | GNQWVGYDDQESVKSK |
| 52 | 328–343 | YDDQESVKSKVQYLKD |
| 53 | 334–349 | VKSKVQYLKDRQLAGA |
| 54 | 340–355 | YLKDRQLAGAVVWALD |
| 55 | 346–361 | LAGAMVWALDLDDFQG |
| 56 | 352–377 | WALDLDDFQGSFCGQD |
| 57 | 358–373 | DFQGSFCGQDLRFPLT |
| 58 | 364–379 | CGQDLRFPLTNAIKDA |
| 59 | 368–383 | LRFPLTNAIKDALAAT |

Peptide HLA-DR Binding Assay

DR4 (DRB1*0401) and DR4 (DRB1*0404) molecules were purified from the homozygous EBV-transformed human B lymphoblastoid cell lines Huly138IC2 and BM92 using the mAb t243, directed against a monomorphic determinant on the DR-complex (Lampson, L. A and R. Levy (1980), J. Immunol. 125:293 299).

The peptide binding studies were performed using a semi-quantitative competition binding assay (Joosten et al 1994, Int. Immunol. 6, 751). Briefly, purified HLA-DR molecules (30 nM DR4(DRB1*0401) or 15 nM DR4 (DRB1*0404) were incubated at pH5.0 with 50 nM biotinylated marker peptide (HA $309_{y \to F}$) and a concentration range of competitor peptide in a final volume of 25 μl binding buffer (PBS containing 0.01% Na$_3$, 0.05% NP-40, 5% DMSO, 1 mM AEBSF, 1 mM N-ethyl maleimide, 8 mM EDTA and 10 μm pepstatin A). After 44 hr of incubation at RT, HLA DR bound marker peptide was separated from free marker peptide using a 96 well vacuum dotblot apparatus (Hybri. dot, BRL) and a nitrocellulose membrane (Hybond ECL, Amersham, UK). The nitrocellulose filters were blocked with 0.5% DNA blocking reagent (Boehringer) in 0.1 M maleic acid, 150 mM NaCl, pH7.5.

After 0.5–1 hr, the filters were washed in PBS, 0.05% Tween 20 (Sigma) and incubated with Strepcavidin-HRPO (Southern Biotechnology) in a 1:10.000 dilution. Biotinylated peptides were detected by enhanced chemiluminescence using a Western Blot ECL kit (Amersham). Exposure of the preflashed films (Hyperfilm-ECL, Amersham) was for 10 min. The spots were analysed by scanning the films and using Image Quant/Excel software for analysis.

The affinity of a given peptide for binding DRB1*0401-encoded molecules was related to competition with the marker peptide. This relative binding affinity was defined as the peptide concentration at which the signal was reduced to 50% (IC$_{50}$).

Proliferative Responses of Blood Mononuclear Cells

In order to identify T-cell epitopes within HC gp-39, 59 peptides of 16 AA in length, overlapping by 10 AA were tested for their capacity to induce a proliferative response in PBMC from RA patients and healthy controls carrying the DR4 (DRB1*0401) specificity (Table 1). Table 2 enlists the sequences of the peptides tested.

PBMC obtained from heparinized venous peripheral blood were isolated by standard centrifugation on a Ficoll-Paque gradient. Cells were cultured in four-fold at a concentration of 1,5×10$^5$ cells/well in medium supplemented with 10% heat-inactivated, autologous plasma, L-glutamine, 2-ME and antibiotics in flatbottomed microtiter plates. Cells were incubated in medium alone or in the presence of phytohaemagglutinin (PHA) (2:5 μg/ml) to assert cell viability, or in the presence of 10 or 100 μg/ml of the HC gp-39-derived peptides. In several cases, sets of 2 or 3 sequential peptides were tested due to limited PBMC numbers of individual donors. Cultures were incubated in a total volume of 210 μl for 7 days at 370° C. in a humidified atmosphere of 5% CO$_2$. Cultures were pulsed during the last 18 hours with 0.25 μCi $^3$H-thymidine ([$^3$H]TdR). Cells were harvested on glassfiber filters and [$^3$H] TdR incorporation was measured by gas scintillation (Packard Matrix 96 βcounter). Only peptides inducing a proliferative response at both 10 and 100 μg/ml were considered to contain a T-cell epitope. Responses were defined positive if stimulation index values (SI, antigen-specific counts per 5 min (cp5 m)/background cp5 m) exceeded or equaled 2.

Results

Identification of T-Cell Epitopes by Proliferative Responses of Blood Mononuclear Cells T-cell reactivity to HC gp-39-derived peptide as analyzed by measuring the PBMC proliferative response in DR4 (DRB1*0401)-positive RA patients and healthy donors. Proliferative responses were tested in autologous plasma. In Table IIIA and IIIB the results of 7 experiments are presented showing the responses of RA patients (Table IIIA) and the responses of healthy donors (Table IIIB) to 59 overlapping sequences derived from HC gp-39. Donors found to respond to both concentrations (100 and 10 μg/ml) of a peptide were ranked as responders and donors which did not respond to both concentrations tested were ranked as non-responders (NR).

Responses to the individual peptides 1, 2, 5, 6, 12, 15, 30, 34, 37, 38, 40, 41, 54 and 55 (the numbers respond to the respective SEQ ID NO of each peptide, for example, peptide 30 means: peptide having amino acid sequence of SEQ ID NO:30) were observed in one or more donors, thereby identifying these sequences as T-cell epitopes.

Interestingly, responses to peptides 2, 34, 38, 40, 54 and 55 were observed in RA patients only.

On the other hand, peptides 12 and 41 induced only responses in healthy donors (230, 235) thus far.

In addition, as can be seen in Table 3, responses were found to the following sets of: peptides 1/2, 1/2/3, 4/5/6, 5/6, 15/16, 17/18, 19/20, 28/29/30, 29/30, 37/38, 37/38/39, 39/40, 46/47/48, 53/54, 55/56 and 55/56/57. These results are in accordance with most of the results of the individual peptides mentioned above. Moreover, the responses against the sets of peptides define regions that contain additional T-cell epitopes, i.e. the regions covered by peptides 16–20 (residu 112–151), 28–29 (residu 184–205), 38–40 (residu 244–271), 46–48 (residu. 292–319) and 53–57 (334–373).

Six out of 7 DR4 (DRB1*0401)-positive RA patients responded to HC gp-39-derived peptides or sets of peptides and were therefore ranked as responders. In the healthy donor group (HD), 3 out 5 donors were ranked as responders. In general, RA patients appeared to respond to many more HC gp-39 regions than healthy donors (healthy donor 230 being an exception) For example, PBMC from RA patient 272, which were tested against individual peptides, appeared to respond to a total of 11 peptides (1, 2, 5, 6, 30, 34, 37, 38, 40, 54 an 55). PBMC of the other patients (patient 287 being an exception) showed responses against sets of peptides overlapping these 11 sequences and identified some additional regions containing T-cell epitopes (peptides 14–20 and 46–48).

PBMC derived from a healthy donor (230) further confirmed the presence of T-cell epitopes in peptides 1, 5, 6, 15, 30 and 37.

Overall, the peptides or sets of peptides most frequently recognized contain peptides 1/2, 5/6, 30, 37/38, 54/55).

Correlation of T-cell Epitopes and DRB4 (DRB1*0401) Binding

Peptides 1, 2, 5, 6, 12, 15, 30, 34, 37, 38, 40, 41, 54 and 55 were all found to stimulate peripheral blood derived T-cells. As a corrollary to this finding, all of these peptides were found to bind to DR4 (DRB1*0401) with relatively high affinity (except peptides 2 and 38 which bind with intermediate relative affinity). Peptides 3, 4, 16, 17, 18, 19, 20, 28, 29, 39, 46, 47, 48, 53, 56 and 57 were tested in sets rather than individually. It is very likely that several of these peptides also contain relevant T-cell epitopes. In any case, these peptides all can-bind DRB4 (DRB1*0401) with high to intermediate relative affinity (except for peptide 20 which binds with poor relative affinity).

TABLE IIIA

Peptide-induced proliferative responses of PBMC from RA patients.

| peptide | 272 0401 R | 262 0401 R | 276 0401 R | 286 0401 R | 191 0401 R | 287 0401 NR | 259 0401 R | 0401 binding |
|---|---|---|---|---|---|---|---|---|
| 1 | pos | | | | | | | +++ |
| 2 | pos | | pos | pos | pos | | pos | + |
| 3 | | | | | | | | + |
| 4 | | | | | | | | + |
| 5 | pos | | | | | | pos | +++ |
| 6 | pos | | pos | pos | | | | +++ |
| 7 | | | | | | | | |
| 8 | | | | | | | | |
| 9 | | | | | | | | |
| 10 | | | | | | | | |
| 11 | | | | | | | | |
| 12 | | | | | | | | |
| 13 | | | | | | | | |
| 14& | | | | | | | | |
| 15& | | | | | | | | +++ |
| 16 | | | | | pos | | | +++ |
| 17 | | | | | | | | ++ |
| 18 | | | pos | | | | | + |
| 19 | | | | | | | | + |
| 20 | | | | | pos | | | +/− |
| 21 | | | | | | | | |
| 22 | | | | | | | | |
| 23 | | | | | | | | |
| 24 | | | | | | | | |
| 25 | | | | | | | | |
| 26 | | | | | | | | |
| 27 | | | | | | | | |
| 28 | | | | | | | | +++ |
| 29 | | | | | | pos | | +++ |
| 30 | pos | pos | pos | pos | | | | +++ |
| 31 | | | | | | | | |
| 32 | | | | | | | | |
| 33 | | | | | | | | |
| 34 | pos | | | | | | | +++ |
| 35 | | | | | | | | |
| 36 | | | | | | | | |
| 37 | pos | | | | | | | +++ |
| 38 | pos | pos | pos | pos | | | pos | + |
| 39 | | | | | | | | ++ |
| 40& | pos | | | pos | | | | +++ |
| 41& | | | | | | | | |
| 42 | | | | | | | | |
| 43 | | | | | | | | |
| 44 | | | | | | | | |
| 45 | | | | | | | | |
| 46 | | | | | | | | +++ |
| 47 | | | | | | pos | | +++ |
| 48 | | | | | | | | + |
| 49 | | | | | | | | |
| 50 | | | | | | | | |
| 51& | | | | | | | | |
| 52& | | | | | | | | |
| 53 | | | | | | | | +++ |
| 54 | pos | | pos | pos | | | | +++ |
| 55 | pos | | | | | | | +++ |
| 56 | | | | | pos | pos | | +++ |
| 57 | | | | | | | | ++ |
| 58 | | | | | | | | |
| 59 | | | | | | | | |
| BG | 0.2 | 0.7 | 0.5 | 0.8 | 2.4 | 0.9 | 0.2 | | pos=positive responses to both 100 and 10 microgram/ml of peptide or sets of peptides (SI≧2 were regarded positive). Together the pep tides (16 AA in length and overlapping by 10 AA) cover the complete mature sequence of mature HC gp-39 (residu 22–383). Peptides were synthesized at Eurosequence (Groningen, The Netherlands). RA=rheumatoid arthritis patient. 0401=donor carrying the RA associated HLA-DR1*0401 specificity. NR=non-responder. R=responder. BG=mean of background counts per 5 minutes×10 measured in wells without antigen. +++=high affinity binder (IC50<1 µM), ++=good affinity binder (1<IC50<10 µM); +=intermediate binder (10<IC50<100 µM); +/−=poor binder (100<IC50<1000 µM); −=non-binder (IC50>1000 µM)

TABLE IIIB

Peptide-induced proliferative responses of PBMC from healthy donors.

| HD peptide | 155 0401 R | 157 0401 NR | 168 0401 NR | 230 0401 R | 235 0401 R | 0401 binding |
|---|---|---|---|---|---|---|
| 1 | | | | pos | | +++ |
| 2 | | | | | | |
| 3 | | | | | | |
| 4 | | | | | | |
| 5 | | | | pos | | +++ |
| 6 | | | | pos | | +++ |
| 7 | | | | | | |
| 8 | | | | | | |
| 9 | | | | | | |
| 10 | | | | | | |
| 11 | | | | | | |
| 12 | | | | pos | | +++ |

TABLE IIIB-continued

Peptide-induced proliferative responses of PBMC from healthy donors.

| HD peptide | HD 155 0401 R | HD 157 0401 NR | HD 168 0401 NR | HD 230 0401 R | HD 235 0401 R | 0401 binding |
|---|---|---|---|---|---|---|
| 13 | | | | | | |
| 14& | | | | | | |
| 15& | | | | pos | | +++ |
| 16 | | | | | | |
| 17 | | | | | | |
| 18 | | | | | | |
| 19 | | | | | | |
| 20 | | | | | | |
| 21 | | | | | | |
| 22 | | | | | | |
| 23 | | | | | | |
| 24 | | | | | | |
| 25 | | | | | | |
| 26 | | | | | | |
| 27 | | | | | | |
| 28 | | | | | | |
| 29 | | | | | | |
| 30 | | | | pos | | +++ |
| 31 | | | | | | |
| 32 | | | | | | |
| 33 | | | | | | |
| 34 | | | | | | |
| 35 | | | | | | |
| 36 | | | | | | |
| 37 | pos | | | pos | pos | +++ |
| 38 | | | | | | |
| 39 | | | | | | |
| 40 | | | | | | |
| 41 | | | | | pos | +++ |
| 42 | | | | | | |
| 43 | | | | | | |
| 44 | | | | | | |
| 45 | | | | | | |
| 46 | | | | | | |
| 47 | | | | | | |
| 48 | | | | | | |
| 49 | | | | | | |
| 50 | | | | | | |
| 51 | | | | | | |
| 52 | | | | | | |
| 53 | | | | | | |
| 54 | | | | | | |
| 55 | | | | | | |
| 56 | | | | | | |
| 57 | | | | | | |
| 58 | | | | | | |
| 59 | | | | | | |
| BG | 4, 2 | 10, 4 | 2, 2 | 3, 6 | 3, 5 | | pos=positive responses to both 100 and 10 microgram/ml of peptide or sets of peptides (SI>2 were regarded positive). Together the peptides (16 AA in length and overlapping by 10 AA) cover the complete mature sequence of mature HC gp-39 (residu 22–383). Peptides were synthesized at Eurosequence (Groningen, The Netherlands). HD=healthy donor. 0401=donor carrying the RA-associated HLA-DRB1*0401 specificity. NR=non-responder. R=responder. BG=mean of background counts per 5 minutes×10$^{-3}$ measured in wells without antigen. +++=high affinity binder (IC50<1 $\mu$M); ++=good affinity binder (1<IC50<10 $\mu$M); +=intermediate binder (10<IC50<100 $\mu$M); +/−=poor binder (100<IC50<1000 $\mu$M); −=non-binder (IC50>1000 $\mu$M)

Abbreviations
AEBSF: 4-(2-AminoEthyl)-BenzeneSulfonyl Fluoride
BB: binding buffer
BCA: Bicinchoninic Acid
BSA: bovine serum albumin
DMSO: Dimethyl Sulfoxide
ECL: Enhanced Chemiluminescence
EDTA: EthyleneDiamine Tetra Acetic acid
FACS: Fluorescence Activated Cell Sorter
HLA: Human Leukocyte Antigens
HPLC: High Pressure Liquid Chormtatography
HRP: Horse Radish Peroxidase
MHC CLASS II: Major Histocompatibility Complex class II
NMR: Nuclear Magnetic Resonance
NP-40: Nonidet P-40
PBS: Phosphate Buffered Saline
PVDF: Polyvinylidene difluoride
RA: Rheumatoid Arthritis
SDS-PAGE: Sodium DodecylSulfate Polyacrylamide Gel Electrophoresis

What is claimed is:

1. A peptide consisting of 16 to 55 amino acid residues, comprising the amino acid sequence YKLVCYYTSWSQYREG (SEQ ID NO: 1).

2. A pharmaceutical composition comprising a peptide according to claim 1, and a pharmaceutically acceptable carrier.

3. A test kit for use in the detection of activated autoreactive T cells, comprising a peptide according to claim 1.

4. A pharmaceutical composition consisting of one or more peptides selected from the group consisting of peptides consisting of 16 to 55 amino acid residues and comprising the amino acid sequence YKLVCYYTSWSQYREG (SEQ ID NO:1).

5. A method of inducing systemic immunological tolerance, comprising administering mucosally to a patient in need thereof a pharmaceutical composition comprising one or more peptides containing 16 to 55 amino acid residues selected from the group consisting of the amino acid sequence LVCYYTSWS (SEQ ID NO:60) and a pharmaceutically acceptable carrier.

6. A method for inducing a systemic immunological tolerance, comprising administering muscosally to a patient in need thereof a pharmaceutical composition according to claim 4.

* * * * *

SEQUENCE LISTING

<160> NUMBER OF SEQ ID NOS: 78

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 1

Tyr Lys Leu Val Cys Tyr Tyr Thr Ser Trp Ser Gln Tyr Arg Glu Gly
 1               5                   10                  15

```
<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 2

Tyr Thr Ser Trp Ser Gln Tyr Arg Glu Gly Asp Gly Ser Cys Phe Pro
 1               5                  10                  15

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 3

Tyr Arg Glu Gly Asp Gly Ser Cys Phe Pro Asp Ala Leu Asp Arg Phe
 1               5                  10                  15

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 4

Ser Cys Phe Pro Asp Ala Leu Asp Arg Phe Leu Cys Thr His Ile Ile
 1               5                  10                  15

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 5

Leu Asp Arg Phe Leu Cys Thr His Ile Ile Tyr Ser Phe Ala Asn Ile
 1               5                  10                  15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 6

Thr His Ile Ile Tyr Ser Phe Ala Asn Ile Ser Asn Asp His Ile Asp
 1               5                  10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN
```

```
<400> SEQUENCE: 7

Phe Ala Asn Ile Ser Asn Asp His Ile Asp Thr Trp Glu Trp Asn Asp
 1               5                  10                  15

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 8

Asp His Ile Asp Thr Trp Glu Trp Asn Asp Val Thr Leu Tyr Gly Met
 1               5                  10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 9

Glu Trp Asn Asp Val Thr Leu Tyr Gly Met Leu Asn Thr Leu Lys Asn
 1               5                  10                  15

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 10

Leu Tyr Gly Met Leu Asn Thr Leu Lys Asn Arg Asn Pro Asn Leu Lys
 1               5                  10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 11

Thr Leu Lys Asn Arg Asn Pro Asn Leu Lys Thr Leu Leu Ser Val Gly
 1               5                  10                  15

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 12

Pro Asn Leu Lys Thr Leu Leu Ser Val Gly Gly Trp Asn Phe Gly Ser
 1               5                  10                  15
```

```
<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 13

Leu Ser Val Gly Gly Trp Asn Phe Gly Ser Gln Arg Phe Ser Lys Ile
 1               5                  10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 14

Asn Phe Gly Ser Gln Arg Phe Ser Lys Ile Ala Ser Asn Thr Gln Ser
 1               5                  10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 15

Phe Ser Lys Ile Ala Ser Asn Thr Gln Ser Arg Arg Thr Phe Ile Lys
 1               5                  10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 16

Asn Thr Gln Ser Arg Arg Thr Phe Ile Lys Ser Val Pro Pro Phe Leu
 1               5                  10                  15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 17

Thr Phe Ile Lys Ser Val Pro Pro Phe Leu Arg Thr His Gly Phe Asp
 1               5                  10                  15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN
```

```
<400> SEQUENCE: 18

Pro Pro Phe Leu Arg Thr His Gly Phe Asp Gly Leu Asp Leu Ala Trp
 1               5                  10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 19

His Gly Phe Asp Gly Leu Asp Leu Ala Trp Leu Tyr Pro Gly Arg Arg
 1               5                  10                  15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 20

Asp Leu Ala Trp Leu Tyr Pro Gly Arg Arg Asp Lys Gln His Phe Thr
 1               5                  10                  15

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 21

Pro Gly Arg Arg Asp Lys Gln His Phe Thr Thr Leu Ile Lys Glu Met
 1               5                  10                  15

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 22

Gln His Phe Thr Thr Leu Ile Lys Glu Met Lys Ala Glu Phe Ile Lys
 1               5                  10                  15

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 23

Ile Lys Glu Met Lys Ala Glu Phe Ile Lys Glu Ala Gln Pro Gly Lys
 1               5                  10                  15
```

```
<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 24

Glu Phe Ile Lys Glu Ala Gln Pro Gly Lys Lys Gln Leu Leu Leu Ser
 1               5                  10                  15

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 25

Gln Pro Gly Lys Lys Gln Leu Leu Leu Ser Ala Ala Leu Ser Ala Gly
 1               5                  10                  15

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 26

Leu Leu Leu Ser Ala Ala Leu Ser Ala Gly Lys Val Thr Ile Asp Ser
 1               5                  10                  15

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 27

Leu Ser Ala Gly Lys Val Thr Ile Asp Ser Ser Tyr Asp Ile Ala Lys
 1               5                  10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 28

Thr Ile Asp Ser Ser Tyr Asp Ile Ala Lys Ile Ser Gln His Leu Asp
 1               5                  10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN
```

```
<400> SEQUENCE: 29

Asp Ile Ala Lys Ile Ser Gln His Leu Asp Phe Ile Ser Ile Met Thr
  1               5                  10                  15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 30

Gln His Leu Asp Phe Ile Ser Ile Met Thr Tyr Asp Phe His Gly Ala
  1               5                  10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 31

Ser Ile Met Thr Tyr Asp Phe His Gly Ala Gln Arg Gly Thr Thr Gly
  1               5                  10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 32

Phe His Gly Ala Trp Arg Gly Thr Thr Gly His His Ser Pro Leu Phe
  1               5                  10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 33

Gly Thr Thr Gly His His Ser Pro Leu Phe Arg Gly Gln Glu Asp Ala
  1               5                  10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 34

Ser Pro Leu Phe Arg Gly Gln Glu Asp Ala Ser Pro Asp Arg Phe Ser
  1               5                  10                  15
```

```
<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 35

Gln Glu Asp Ala Ser Pro Asp Arg Phe Ser Asn Thr Asp Tyr Ala Val
 1               5                  10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 36

Asp Arg Phe Ser Asn Thr Asp Tyr Ala Val Gly Tyr Met Leu Arg Leu
 1               5                  10                  15

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 37

Asp Tyr Ala Val Gly Tyr Met Leu Arg Leu Gly Ala Pro Ala Ser Lys
 1               5                  10                  15

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 38

Met Leu Arg Leu Gly Ala Pro Ala Ser Lys Leu Val Met Gly Ile Pro
 1               5                  10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 39

Pro Ala Ser Lys Leu Val Met Gly Ile Pro Thr Phe Gly Arg Ser Phe
 1               5                  10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN
```

```
<400> SEQUENCE: 40

Met Gly Ile Pro Thr Phe Gly Arg Ser Phe Thr Leu Ala Ser Ser Glu
  1               5                  10                  15

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 41

Gly Arg Ser Phe Thr Leu Ala Ser Ser Glu Thr Gly Val Gly Ala Pro
  1               5                  10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 42

Ala Ser Ser Glu Thr Gly Val Gly Ala Pro Ile Ser Gly Pro Gly Ile
  1               5                  10                  15

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 43

Val Gly Ala Pro Ile Ser Gly Pro Gly Ile Pro Gly Arg Phe Thr Lys
  1               5                  10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 44

Gly Pro Gly Ile Pro Gly Arg Phe Thr Lys Glu Ala Gly Thr Leu Ala
  1               5                  10                  15

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 45

Arg Phe Thr Lys Glu Ala Gly Thr Leu Ala Tyr Tyr Glu Ile Cys Asp
  1               5                  10                  15
```

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 46

Gly Thr Leu Ala Tyr Tyr Glu Ile Cys Asp Phe Leu Arg Gly Ala Thr
 1               5                  10                  15

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 47

Glu Ile Cys Asp Phe Leu Arg Gly Ala Thr Val His Arg Thr Leu Gly
 1               5                  10                  15

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 48

Arg Gly Ala Thr Val His Arg Thr Leu Gly Gln Gln Val Pro Tyr Ala
 1               5                  10                  15

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 49

Arg Thr Leu Gly Gln Gln Val Pro Tyr Ala Thr Lys Gly Asn Gln Trp
 1               5                  10                  15

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 50

Val Pro Tyr Ala Thr Lys Gly Asn Gln Trp Val Gly Tyr Asp Asp Gln
 1               5                  10                  15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN -continued

```
<400> SEQUENCE: 51

Gly Asn Gln Trp Val Gly Tyr Asp Asp Gln Glu Ser Val Lys Ser Lys
  1               5                  10                  15

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 52

Tyr Asp Asp Gln Glu Ser Val Lys Ser Lys Val Gln Tyr Leu Lys Asp
  1               5                  10                  15

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 53

Val Lys Ser Lys Val Gln Tyr Leu Lys Asp Arg Gln Leu Ala Gly Ala
  1               5                  10                  15

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 54

Tyr Leu Lys Asp Arg Gln Leu Ala Gly Ala Met Val Trp Ala Leu Asp
  1               5                  10                  15

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 55

Leu Ala Gly Ala Met Val Trp Ala Leu Asp Leu Asp Asp Phe Gln Gly
  1               5                  10                  15

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 56

Trp Ala Leu Asp Leu Asp Asp Phe Gln Gly Ser Phe Cys Gly Gln Asp
  1               5                  10                  15
```

```
<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 57

Asp Phe Gln Gly Ser Phe Cys Gly Gln Asp Leu Arg Phe Pro Leu Thr
 1               5                  10                  15

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 58

Cys Gly Gln Asp Leu Arg Phe Pro Leu Thr Asn Ala Ile Lys Asp Ala
 1               5                  10                  15

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 59

Leu Arg Phe Pro Leu Thr Asn Ala Ile Lys Asp Ala Leu Ala Ala Thr
 1               5                  10                  15

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 60

Leu Val Cys Tyr Tyr Thr Ser Trp Ser
 1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 61

Phe Leu Cys Thr His Ile Ile Tyr Ser
 1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN
```

```
<400> SEQUENCE: 62

Ile Ile Tyr Ser Phe Ala Asn Ile Ser
 1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 63

Leu Lys Thr Leu Leu Ser Val Gly Gly
 1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 64

Phe Ile Lys Ser Val Pro Pro Phe Leu
 1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 65

Phe Asp Gly Leu Asp Leu Ala Trp Leu
 1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 66

Leu Tyr Pro Gly Arg Arg Asp Lys Gln
 1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 67

Tyr Asp Ile Ala Lys Ile Ser Gln His
 1               5
```

```
<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 68

Leu Asp Phe Ile Ser Ile Met Thr Tyr
  1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 69

Phe Ile Ser Ile Met Thr Tyr Asp Phe
  1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 70

Phe Arg Gly Gln Glu Asp Ala Ser Pro
  1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 71

Tyr Ala Val Gly Tyr Met Leu Arg Leu
  1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 72

Met Leu Arg Leu Gly Ala Pro Ala Ser
  1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN
```

-continued

```
<400> SEQUENCE: 73

Leu Ala Tyr Tyr Glu Ile Cys Asp Phe
 1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 74

Leu Arg Gly Ala Thr Val His Arg Thr
 1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 75

Tyr Leu Lys Asp Arg Gln Leu Ala Gly
 1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 76

Leu Ala Gly Ala Met Val Trp Ala Leu
 1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 77

Val Trp Ala Leu Asp Leu Asp Asp Phe
 1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: DERIVED
      FROM SEQUENCE OF HUMAN CARTILAGE (HC) -39 PROTEIN

<400> SEQUENCE: 78

Leu Asp Leu Asp Asp Phe Gln Gly Ser
 1               5
```